United States Patent [19]

Löhn

[11] Patent Number: 4,968,249

[45] Date of Patent: Nov. 6, 1990

[54] DENTAL SPRAY HANDPIECE

[75] Inventor: Gerd Löhn, Biberach/Rissegg, Fed. Rep. of Germany

[73] Assignee: Kaltenbach & Voigt GmbH & Co., Biberach an der Riss, Fed. Rep. of Germany

[21] Appl. No.: 250,326

[22] Filed: Sep. 27, 1988

[30] Foreign Application Priority Data

Oct. 14, 1987 [DE] Fed. Rep. of Germany ....... 3734860

[51] Int. Cl.⁵ ............................................ A61G 17/02
[52] U.S. Cl. ..................................................... 433/80
[58] Field of Search ....................... 433/80, 81, 82, 86, 433/89, 101, 29, 32

[56] References Cited

U.S. PATENT DOCUMENTS

| | | | |
|---|---|---|---|
| 3,137,297 | 6/1964 | Maurer et al. | 433/80 |
| 4,341,518 | 7/1982 | Wallace | 433/29 |
| 4,759,712 | 7/1988 | Demand | 433/80 |
| 4,770,632 | 9/1988 | Ryder et al. | 433/80 |

FOREIGN PATENT DOCUMENTS

| | | |
|---|---|---|
| 1541226 | 8/1968 | Fed. Rep. of Germany . |
| 2021540 | 11/1971 | Fed. Rep. of Germany . |
| 2920009 | 5/1979 | Fed. Rep. of Germany . |
| 2821710 | 11/1979 | Fed. Rep. of Germany ........ 433/80 |
| 3034930 | 4/1982 | Fed. Rep. of Germany . |
| 3337166 | 4/1985 | Fed. Rep. of Germany . |
| 375483 | 4/1964 | Switzerland .......................... 433/32 |
| 228934 | 10/1925 | United Kingdom .................. 433/81 |

*Primary Examiner*—Cary E. Stone
*Attorney, Agent, or Firm*—Scully, Scott, Murphy & Presser

[57] ABSTRACT

A dental spray handpiece, consisting of a switchless sleeve having a media inlet connection at its rearward end and a media discharge outlet at its forward end. Within the sleeve there is arranged at least one media conduit leading from the media connection to the media discharge outlet and discharging therefrom at this location, with a remote-controlled flow of media.

8 Claims, 1 Drawing Sheet

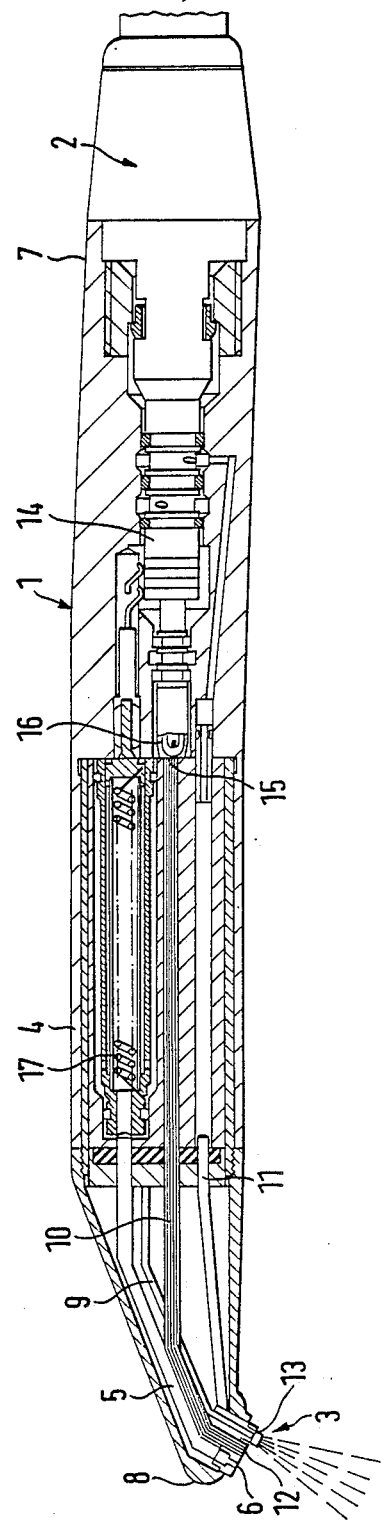

DENTAL SPRAY HANDPIECE

BACKGROUND OF THE INVENTION

1. Field of the Invention

The present invention relates to a dental spray handpiece, consisting of a switchless sleeve having a media inlet connection at its rearward end and a media discharge outlet at its forward end; in which sleeve there is arranged at least one media conduit leading from the media inlet connection to the media discharge outlet and discharging outwardly therefrom at this location, with a remote-controlled flow of media.

As the media, the conduits can convey, for example, air or water.

2. Discussion of the Prior Art

A spray handpiece of that type is known from the disclosure of German Laid-Open Patent Appln. No. 20 21 540. In this known spray handpiece, arranged on the forward end of the sleeve is an extension cannula which, initially, extends in the direction of the longitudinal axis of the sleeve and then possesses a bent or angled forward end piece, on the free end of which the media discharge outlet is axially located.

In a spray handpiece of that type, similar as with a spray handpiece which has become known from the disclosure of German Laid-Open Patent Appln. No. 30 34 930, there is encountered the endeavor that the treating personnel holds the spray handpiece in the hand as he would a pencil, in order to avoid any change-over by the treating personnel during a transfer from a dental treatment handpiece, such as a dental drill handpiece, to a spray handpiece.

In that connection, it has been ascertained that in the known spray handpiece, the bent cannula with its axial media discharge outlet will mislead the treating personnel so as not to grip and hold the spray handpiece like a pencil, such as would be inherently desirable, but as heretofore; for example, such as would be usual for a spray handpiece pursuant to German Patent No. 15 51 226, rather like a pistol, and namely to be able to better approach with the media discharge outlet the location in the mouth of the patient which is to be cooled or cleaned.

SUMMARY OF THE INVENTION

The invention as described hereinbelow, provides for a dental spray handpiece of the type under consideration, which is designed to eliminate the disadvantages encountered in the prior art, in that the sleeve is constructed in the type of a freely elongated crayon, and wherein the media discharge outlet of the media conduit is constructed as an outlet orifice directed radially towards the side of the sleeve and communicating outwardly from the wall structure of the sleeve. With regard to the foregoing, with a much greater degree of certainty, there is an assurance that the treating personnel will, upon the grasping handling of a spray handpiece, grip and hold onto the spray handpiece just as well as a tooth-treating handpiece like a kind of a pencil, so as to securely avoid any changeover during a transfer from one to the other type of handpiece.

The advantages which are achieved by means of the present invention can be essentially ascertained in that, because of the configuration of the sleeve as a freely elongated crayon, there is obtained a through-extending straight handpiece; in essence, extending from the media inlet connection to the radial media discharge outlet, whereby the handpiece, so to say, must necessarily be gripped and held by the treating personnel, such as a dental treating handpiece; in effect, a dental drill handpiece in the type of a pencil. Through the special configuration and arrangement of the media discharge outlet there is achieved that even during the remote-control operation; for example, media discharge by means of hand or foot-operated switch control, the treating personnel will continue to hold the spray handpiece in the manner of a pencil. Thus, with regard to the gripping technique, the treating personnel, with assurance, is not subjected to any kind of change-over during a transfer from a tooth-treating handpiece to a spray handpiece.

BRIEF DESCRIPTION OF THE DRAWINGS

Reference may now be had to the following detailed description of an exemplary embodiment of the invention, taken in conjunction with the accompanying single figure of drawing showing a longitudinal sectional view of a dental spray handpiece.

DETAILED DESCRIPTION OF THE PREFERRED EMBODIMENT

The illustrated spray handpiece 1 consists of a switchless sleeve 4; in essence, a sleeve devoid of any operating switches, which possesses a media inlet connection at its rearward end 7 and a media discharge outlet 3 at its forward end 8, in which sleeve there are arranged a plurality of media conduits 5, 9, 10, 11 leading from the media inlet connection 2 to the media discharge outlet 3 and discharging to the outside therefrom. The flow of the collective media which stream through the media conduits 5, 9, 10, 11 is remote-controlled; for example, controlled through a foot-operated switch.

The sleeve 4 is constructed in the type of a slender freely elongated crayon or pencil-like member, whereby the media discharge outlet 3 of each of the media conduits 5, 9, 10, 11 is respectively constructed as an outlet orifice 6, 12, 13 directed radially towards the side of the sleeve 4 and opening outwardly from the wall structure of the sleeve.

Basically, there can also be provided fewer media conduits in the spray handpiece; for instance, only a single media conduit.

The axis of the respective outlet orifice 6, 12, 13 is slightly angled or sloped towards the neighboring forward end 8 of the sleeve 4. As a result thereof, this will enhance the advantageous effect; namely, that the treating personnel will practically automatically grip the spray handpiece in a kind of pencil grip, and also during the treatment; in essence, during the discharge of media, will continue to hold it in the manner of a pencil. The same purpose is served when, as illustrated, the three outlet orifices 6, 12, 13 are arranged along a cylindrical line or generatrix about the essentially cylindrical sleeve 4.

The media conduits are formed by a warm blown-air conduit 5, a water conduit 9, a light-conductor 10, and a spray-air conduit 11, whereby the outlets for the water conduit 9 and the spray-air conduit 11 are joined into a common outlet orifice 13 producing a spray discharge. It is also possible to provide for an actuation pursuant to which only water will be discharged from the common outlet orifice 13.

The above-mentioned arrangement of the three outlet orifices 6, 12, 13 is, in detail, provided in such a manner that the outlet orifice 6 for the warm blown-air line conduit 5 is located closest to the forward end 8 of the sleeve 4, and that there then follows the outlet orifice 12 for the light-conductor 10, whereupon there follows the combined outlet orifice 13 for the water conduit 9 and the spray-air conduit 11.

The elucidated intended purpose is achieved in a still better manner when, as represented, the outlet orifices are axially-parallel, and the angle formed by a perpendicular plane relative to the longitudinal axis 14 of the sleeve 4 extending through the axes of the outlet orifices 6, 12, 13 is greater than the angle formed by the outlet orifices 6, 12, 13 and the axis 14 of the sleeve 4 in this region.

The light-conductor 10 is formed by a light-transmitting line which terminates in an open end within the sleeve 4, and the free end 15 of which has a light-supplying element 16 associated therewith. The light-power element 16 is formed by an incandescent lamp or lightbulb which is connected to an electrical current supply circuit (not shown); preferably a halogen lamp.

As can be ascertained from the drawing, the warm blown-air conductor 5 has a heating device 17 preferably formed from an electrical heating filament, associated therewith, and which heats the air which is conveyed to the conduit 5.

What is claimed is:

1. Dental spray handpiece comprising a switchless sleeve having a media inlet connection at a rearward end and a media discharge outlet at a forward end; at least one media conduit in said sleeve extending from the media inlet connection to the media discharge outlet and discharging outwardly thereof with a remote-controlled flow of media; said sleeve being configured as a freely elongated crayon-like member, said media discharge outlet of the media conduit forming an outlet orifice directed radially towards the side of said sleeve and discharging outwardly from the wall structure of said sleeve, said media conduit comprising a plurality of conduits arranged in said sleeve, each said conduit having an outlet orifice forming a media discharge outlet radially directed towards the side of said sleeve, wherein said media conduits include a warm blow-air conduit, a water conduit, a light-conductor, and a spray air conduit, said outlet orifices being arranged axially-parallel, and an angle formed by a perpendicular plane relative to the longitudinal axis of said sleeve extending through the axes of said outlet orifices is greater than the angle formed by said outlet orifices and said longitudinal axis of the sleeve.

2. Spray handpiece as claimed in claim 1, wherein the axis of said outlet orifice is slightly angled towards the adjacent forward end of said sleeve.

3. Spray handpiece as claimed in claim 1, wherein the discharges of said water conduit and of said spray air conduit are joined into a single outlet orifice.

4. Spray handpiece as claimed in claim 3, wherein said outlet orifices are arranged in sequence along a cylindrical line on said sleeve.

5. Spray handpiece as claimed in claim 4, wherein the outlet orifice of the warm blown-air conduit is located closest to the forward end of said sleeve, followed by the outlet orifice of the light-conductor, and thereafter followed by the joint outlet orifice for the water conduit and the spray air conduit.

6. Spray handpiece as claimed in claim 1, wherein said light-conductor comprises a light element terminating in a free end within said sleeve; and a light-producing element being associated with said free end of said conductor.

7. Spray handpiece as claimed in claim 6, wherein the light-producing element comprises an incandescent lamp, such as a lightbulb or halogen lamp.

8. Spray handpiece as claimed in claim 1, wherein said warm blown-air conduit has heating means associated therewith for heating the air conveyed to said conduit.

* * * * *